United States Patent [19]
Davis et al.

[11] Patent Number: 5,421,810
[45] Date of Patent: Jun. 6, 1995

[54] ORTHOPEDIC HINGE ASSEMBLY FOR AN ORTHOPEDIC BRACE

[75] Inventors: Kenneth P. Davis, High Wycombe; Peter I. Davis, Sunbury-on-Thames, both of England

[73] Assignee: Orthomerica Products, Inc., Newport Beach, Calif.

[21] Appl. No.: 227,510

[22] Filed: Apr. 14, 1994

[51] Int. Cl.⁶ ............................................... A61F 5/00
[52] U.S. Cl. ........................................ 602/16; 602/26; 602/23
[58] Field of Search .................. 602/5, 16, 18, 23, 24, 602/26

[56] References Cited

U.S. PATENT DOCUMENTS

| | | |
|---|---|---|
| 2,545,843 | 3/1951 | Cohan . |
| 3,528,412 | 9/1970 | McDavid . |
| 3,779,654 | 12/1973 | Horne . |
| 3,902,482 | 9/1975 | Taylor . |
| 4,337,764 | 7/1982 | Lerman . |
| 4,881,299 | 11/1989 | Young et al. . |
| 4,928,676 | 5/1990 | Pansiera . |
| 4,969,452 | 11/1990 | Petrofsky et al. ............... 602/23 X |
| 5,000,170 | 3/1991 | Young et al. . |
| 5,038,765 | 8/1991 | Young et al. . |
| 5,039,247 | 8/1991 | Young et al. . |
| 5,302,169 | 4/1994 | Taylor ............................ 602/26 X |

OTHER PUBLICATIONS

The "ezy wrap 1267" Hinged Knee Brace.
Bledsoe Brace Systems Catalog.
The Sentry Post-Op Knee Brace.
Donjoy Post-Op/Rehab Braces, Nov. 1991.
Donjoy Catalog 1989.
Matrix Medical Corporation CKM Brace #89.
Donjoy R.O.M. 4-Point Splint.
Donjoy Cool R.O.M. Splint.

*Primary Examiner*—Richard J. Apley
*Assistant Examiner*—Linda C. M. Dvorak
*Attorney, Agent, or Firm*—Price, Gess & Ubell

[57] ABSTRACT

A hip orthosis having an upper brace portion for mounting on the pelvic area of a patient and a lower brace portion for mounting on the thigh area of a patient has an interconnecting orthopedic hinge assembly with a housing member having a support surface with a first abutment member and an abductor member movably mounted on the housing member and having a second abutment member to operatively contact the first abutment member, to limit the relative movement of the abductor member in a first rotational direction. The worm gear stop member is rotatably mounted within the housing member and includes a third abutment member to operatively contact the first abutment member to limit the relative movement of the abductor member in a second rotational direction. An adjusting screw member is integrally journalled within the housing member for adjusting the rotatable position of the stop member to define the extent of flexion and extension of the abductor member.

20 Claims, 3 Drawing Sheets

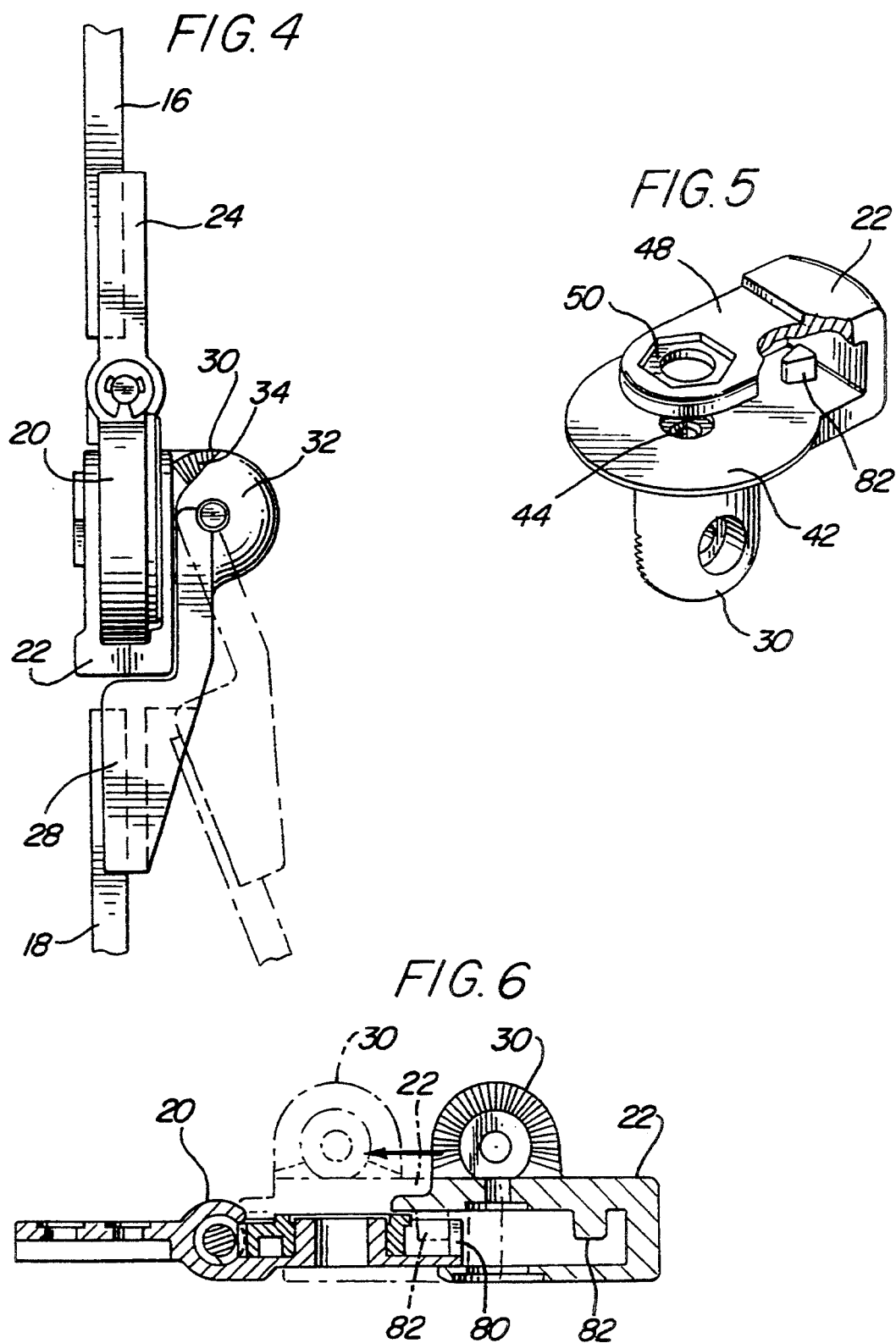

ORTHOPEDIC HINGE ASSEMBLY FOR AN ORTHOPEDIC BRACE

BACKGROUND OF THE INVENTION

1. Field of the Invention

The present invention is directed to an orthopedic hinge assembly for interconnecting an upper portion and a lower portion of a brace and, more particularly, to an improved hinge assembly permitting precise adjustment of the flexion and extension of an abductor member.

2. Description of Related Art

Various forms of orthopedic and orthotic hinge assemblies have been used to interconnect component parts of an orthosis. The orthopedic hinge assemblies are positioned at the joints of a patient to control the limits of movement of a particular limb of the patient, and to support or partially support the weight of the patient across the natural joint of the patient. The brace portions can consist of a cast material, and recently, plastic components, which are usually formed in two separate parts and interconnected by means of a hinge assembly. An example of such a product is a hip orthosis, which is frequently used both for nonoperative treatment of hip disorders and as a prophylaxis to encourage patient compliance with postoperative instructions after a hip arthroplasty. Modular pelvic and thigh components, formed of a polyethylene shell lined with a neoprene material, are interconnected with an aluminum joint having set screws which can be adjustable to permit abduction flexion and extension. This joint assembly basically permits two-dimensional motion of the abductor brace portion and requires the setting of screws to define the movement of the abductor portion, which usually requires the services of a technician in this field.

There is still a demand in the orthopedic field to provide an improved, economically constructed orthopedic hinge assembly.

OBJECTS AND SUMMARY OF THE INVENTION

The present invention provides an orthopedic hinge assembly for interconnecting an upper portion and a lower portion of a brace, such as a hip orthosis, including an upper housing member such as a modular pelvic shell that can be connected to a lower thigh shell. The hinge assembly can be attached to extension plates or bars which, in turn, can be adjustably attached to the respective upper and lower portions of the brace. The housing member includes a cylindrical cavity having a cantilevered stop post integrally cast into the cavity.

An abductor member of the hinge assembly can have a U-shaped housing configuration which also includes a cantilevered stop post extending into the opening of the U-shaped configuration. A partially disc-like stop member is rotatably mounted within the housing cylindrical cavity and between the abductor member, and can include an annular gear member having an abutment face at each end of the gear teeth. An adjusting member can be journalled within a separate cavity of the housing member and includes an operator-adjustable post connected to a helix screw pattern to create a worm gear interconnection with the stop member. The abductor member can support an outer measurement scale to define the degrees of movement for setting the flexion and extension of the abductor member. The abductor member further includes an adjustable bracket member having radially-extending teeth to permit a setting of an abductor plate or bar along a plane perpendicular to the plane of movement of the stop member. An operator can easily and accurately adjust the degree of movement without any additional tools to maintain specific limits of movement for the orthosis. The abductor's bracket member can be offset to enable an axial alignment of its plate or bar with the housing member's attached plate or bar. Alternatively, it can be pivoted to accommodate the desired placement of the brace portions.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 4 is a side view of the orthopedic hinge assembly of the present invention;

FIG. 5 is a perspective partial cross-sectional view of the abductor member of the hinge assembly of the present invention;

FIG. 6 are cross-sectional views of the housing member and abductor member of the hinge assembly of the present invention.

DETAILED DESCRIPTION OF THE PREFERRED EMBODIMENTS

The following description is provided to enable any person skilled in the medical field to make and use the invention and sets forth the best modes contemplated by the inventor of carrying out his invention. Various modifications, however, will remain readily apparent to those skilled in the art, since the generic principles of the present invention have been defined herein specifically to provide an improved hip orthosis having an orthopedic hinge assembly that is easily adaptable.

Figure 1:
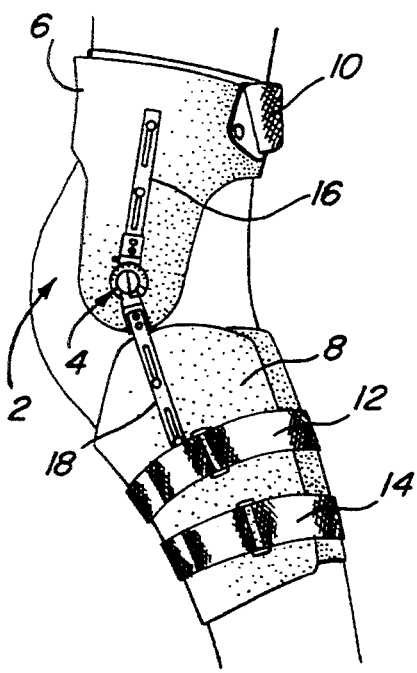
FIG. 1 is a side perspective view of a hip orthosis of the present invention.
Figure 2:
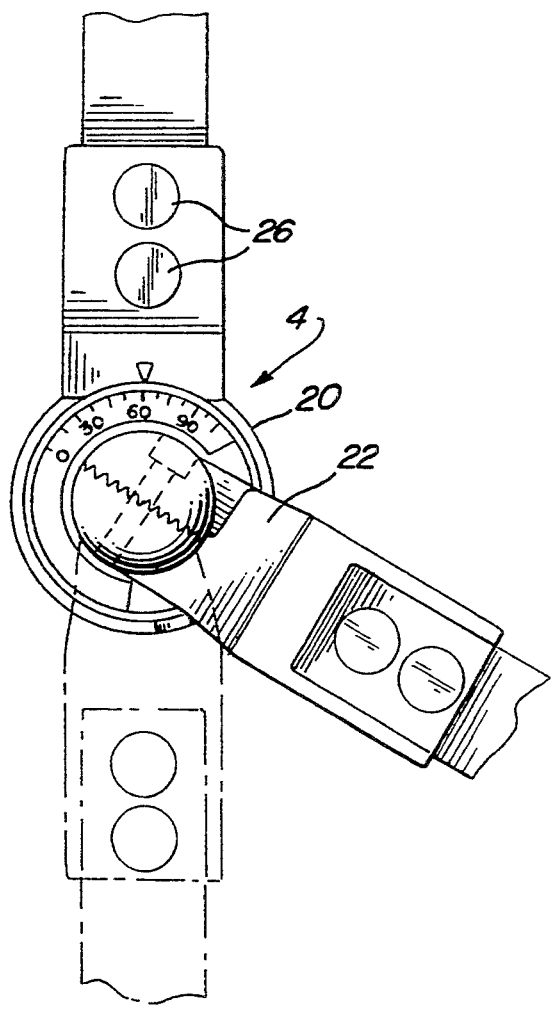
FIG. 2 is a partial plan view of an orthopedic hinge assembly of the present invention.

Referring to FIG. 1, a perspective view of an improved hip orthosis 2 is disclosed using the orthopedic hinge assembly 4 of the present invention. The hip orthosis 2 includes an upper brace portion 6 that can be prefabricated from a perforated polyethylene shell that has been lined with a finished neoprene foam. The upper brace portion 6 in the disclosed embodiment has a configuration for treatment of a right hip ailment such as a patient who has had a total hip arthroplasty. Obviously, the present invention can be modified for a left hip application. The upper brace portion 6 has a left and a right side that are interconnected with a flexible web and can be adjustable with a Velcro TM belt 10 of a conventional hook-and-nap configuration.

The lower brace portion 8 is also formed from a pair of polyethylene shells to capture the outer and inner thigh portions of the patient, the shells are held together by a pair of removably attachable hook-and-nap belts 12 and 14.

The hinge assembly 4 can be attached to metal plates or bars 16 and 18 having elongated slots which, in turn, are directly attached to respective upper brace portion 6 and lower brace portion 8, for example, with rivets. Further description of the upper brace portion 6 and lower brace portion 8 are not believed to be necessary to understand the purpose of the present invention in the environment of a hip orthosis 2. Various modifications of lower and upper brace portions can be made by a person of skill in this field.

The hinge assembly 4 includes a housing member 20 which is attached to an abductor member 22 for relative rotation to an abductor member 22. Both the housing member 20 and the abductor member 22 can be formed from a cast stainless steel part that is machined to desired tolerances. A flange 24 on the housing member 20 has a recessed rectangular surface for interconnection with the plate 16. A pair of rivets 26 can securely fasten the plate 16 to the flange 24. The abductor member 22 has a U-shaped configuration with a semispherical connector member 30 extending outward on one of the legs of the U-shaped configuration. A flange member 28 has an offset complementary semispherical connector member 32 to interface and lock with the connector member 30. The abutting faces of the respective connector members 30 and 32 have radially-extending teeth 34 to permit a firm gripping of the connector members 30 and 32 in an operator-designated position. Respective connector members 30 and 32 have aligned bore openings 36 and 38 for receiving a screw fastener 40, which will lock them together. The bore 36 can have appropriate threads to facilitate the attachment to the screw fastener 40.

Figure 7:
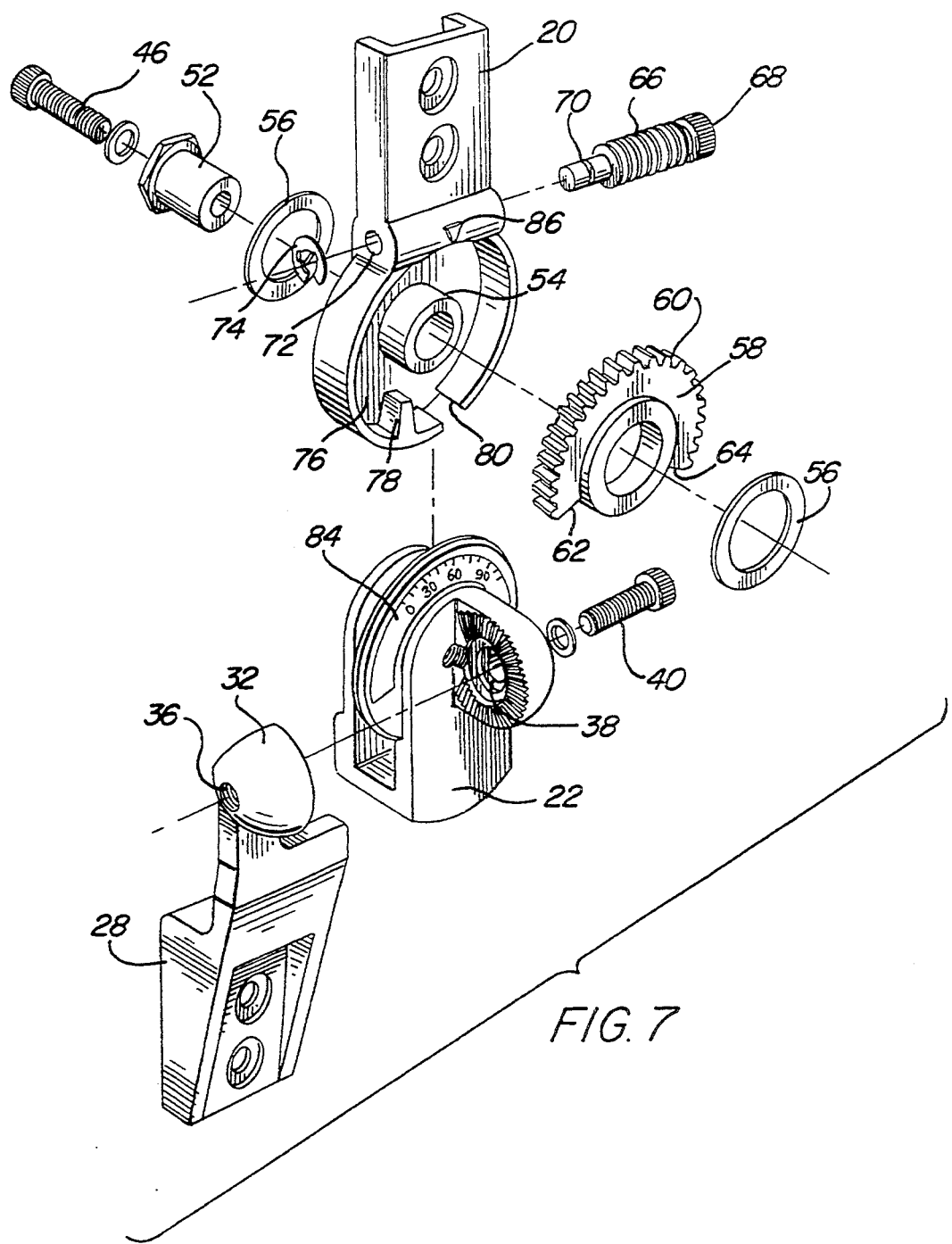
FIG. 7 is an exploded perspective view of the hinge assembly of the present invention.

As can be seen in FIGS. 5 and 7, one of the legs 42 of the U-shaped abductor member has a circular flange configuration with a bore opening 44 being appropriately threaded to receive a threaded fastener 46. The other leg 48 has a hexagonal recessed opening 50 with a central bore to receive a cylindrical bearing member 52 to facilitate the pivoting of the abductor member 22 relative to the housing member 20. The bearing member 52 further extends through a cylindrical support member 54, that is centrally positioned within a cylindrical cavity 76, and is held in place by the fastener 46. A nylatron washer 56 can be mounted to ensure smooth movement. The cylindrical support member 54 is hollow, and its outer surface is machined to provide a bearing surface for a worm wheel or stop member 58. The central axis of the support member 54 provides a common pivotal axis for relative movement of the abductor member and the housing member. The stop member 58 has a hollow bore and a set of teeth 60. At either end of the circularly aligned gear teeth 60 are flat abutment stop faces 62 and 64. These respective stop faces are positioned approximately 144 degrees apart. The gear teeth 60 also have a helix angle of 7 degrees and are compatible with helix screw threads 66 on the adjustment member 68. One end of the adjustment member 68 has an operator adjustment post 70. A lock washer 74 can hold the adjustment member 68 in place within a cavity of the housing member 20 with the post 70 protruding outward from the housing member 20.

Extending radially inward from an outer wall of the cylindrical cavity 76 is an abutment stop member 78. An outer perimeter wall is further apertured to provide an opening 80. The opening 80 is designed to permit the passage of the abutment stop member 82 which is cantilevered upward from the flange leg 42 of the abductor member 22 during assembly of the hinge assembly 4, as shown in FIG. 5. As can be seen in FIG. 6, the abductor member 22 can align its abutment stop member 82 with the opening 80 to permit the assembly of the abductor member 22 onto the housing member 20. This assembly procedure is graphically illustrated in FIG. 6.

The abutment stop face 64 and the housing abutment stop member 78 will define the limits of travel for the abutment stop member 82 on the abductor member 22. In addition, the abutment stop member 58 will be limited in its adjustment travel by contacting the opposite face of the stop member 76 with the abutment stop face 62.

An operator, through rotation of the adjustment post 70, can rotate the worm gear stop member 58 to a desired position to define the movement of the lower brace 8 and, correspondingly, the joint of the patient. To facilitate this alignment, a measurement scale 84 with degrees of rotation can be positioned on the outer flange leg 48 of the abductor member 22, and an indicator mark 86 can be positioned on the exterior surface of the housing member 20.

The flange member 28 has an upper L-shaped configuration to permit it to be offset so that the connector member 32 can be axially connected with the connector member 30. The recessed opening in the flange 28 will align with the recessed opening in the flange member 24 so that the plates 16 and 18 are aligned as shown in FIG. 4.

In assembling the hinge assembly, the housing member 20 has the bearing 52 inserted within the bore of the cylindrical support member 54. The worm gear or stop member 58 is appropriately mounted on the support member 54 within the cylindrical cavity 76. As shown in FIG. 6, the abductor member 22 is aligned with the opening 80 so that the abutment stop member 82 can be positioned within the cylindrical wall of the housing member 20. A fastener 46 secures the hinge assembly together. The operator adjustment member 68 is appropriately inserted within a second cylindrical cavity of the housing member 20 so that the adjustment post 70 extends through the bore 72 and the adjustment member 68 accesses, through a second opening in the perimeter wall, the worm gear 58. A lock washer 74 holds this assembly in place. The flange member 28 is adjustably fastened through its connector member 32 to the connector member 30 of the abductor member 22. A screw fastener 40 permits an adjustment of the flange member 28 so that it rotates in a plane traverse to the rotational movement of the stop member 58. The plates or rod members 16 and 18 can be appropriately fastened by rivets to the flanges 24 and 28. The upper and lower portions of the braces 6 and 8 can be appropriately fastened by rivets to the plate members 16 and 18.

Figure 3:
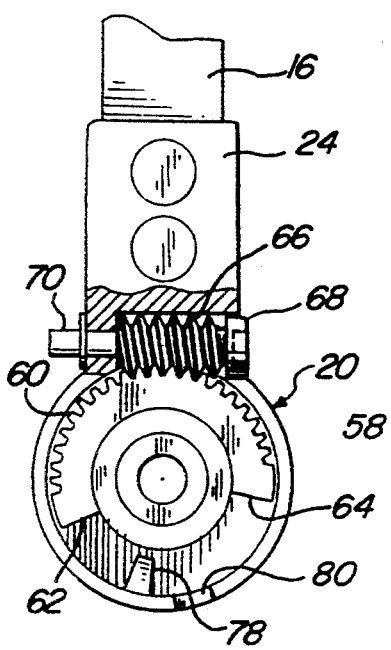
FIG. 3 is a partial cross-sectional view of the housing member and stop member of the present invention.

Referring to FIG. 3, an operator, by rotating the adjustment post 70, can cause the worm gear or stop member 58 to rotate so that abutment stop face 64 will limit, at one end, the movement of the abductor member 22 through contact with the stop member 82. The housing member stop member 78 will limit its movement at the other end of travel. The interface of the abutment stop face 62 with the other side of the stop member 78 limits the travel of the stop member 58 so that its teeth 60 remain in engagement with the helix teeth 66 on the adjustment member 68.

After the upper brace portion 6 has been appropriately affixed to the patient, e.g., a prefabricated configuration can be appropriately adjusted to the patient's body, and the lower brace portion 8 has likewise been adjusted to the thigh of the patient, then the extent of flexion and extension can easily be set through rotation of the adjustment post 70 and monitoring of the scale 84 and indicator 86. There is no requirement of an additional stop member that can be separated from the hinge assembly to be utilized. Neither is there any requirement of additional tools for setting the stop member. The patient can even be instructed to set the limit of travel of the brace member himself or herself by monitoring the scale 84.

While the preferred embodiment of the present invention uses stainless steel castings, it is readily apparent that aluminum or other materials, including plastic, can be used within the scope of the present invention. The hinge assembly 4 is disclosed for a right side of a patient. Appropriate adjustments are made for a left side hinge assembly. The hip orthosis 2 has been shown as the preferred embodiment for incorporating the hinge assembly of the present invention. However, it is readily apparent that other applications of this hinge assembly on orthosis structures for other limbs of a patient can also enjoy the benefits of the present invention.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An orthopedic hinge assembly for interconnecting an upper and a lower portion of a brace, comprising:
   a housing member;
   means on the housing member for enabling attachment to a brace portion;
   an abductor member movably mounted on the housing member;
   means on the abductor member for enabling attachment to another brace portion;
   a stop member rotatably mounted within the housing member;
   means on the housing member for moving and fixing the rotatable position of the stop member relative to the housing member; and
   abutment means for contacting the stop member to define a limit of the relative movement of the abductor member to the housing member.

2. The orthopedic hinge assembly of claim 1 wherein the housing member includes a cylindrical cavity and the abutment means includes a cantilevered stop post extending into the cylindrical cavity.

3. The orthopedic hinge assembly of claim 2 wherein the stop member is mounted within the cylindrical cavity, and includes an annular gear member with teeth and an abutment face at each end of the gear teeth.

4. The orthopedic hinge assembly of claim 2 wherein the cylindrical cavity includes an outer perimeter wall member and the wall member has an opening.

5. The orthopedic hinge assembly of claim 1 wherein the abductor member has a U-shaped configuration that extends around the housing member.

6. The orthopedic hinge assembly of claim 5 wherein the abductor member includes a cantilevered stop post extending into an opening of the U-shaped configuration for engagement with the stop member.

7. The orthopedic hinge assembly of claim 5 wherein the abductor member includes an adjustable bracket member that can pivot relative to the U-shaped configuration.

8. The orthopedic hinge assembly of claim 7 wherein the abductor member and the housing member rotate relative to a common pivotal axis.

9. The orthopedic hinge assembly of claim 1 wherein the means for adjusting includes a screw member.

10. The orthopedic hinge assembly of claim 1, further including a measurement scale on the abductor member and an indicator on the housing member for setting the limits of movement of the abductor member.

11. In a hip orthosis having an upper brace portion for mounting on the pelvic area of a patient and a lower brace portion for mounting on the thigh area of a patient, the improvement comprising:
    a housing member having a support surface with a first abutment member extending therefrom;
    means on the housing member for enabling attachment to one of the upper and lower brace portions;
    an abductor member movably mounted on the housing member and including a second abutment member extending adjacent the support surface to operatively contact the first abutment member to limit the relative movement of the abductor member in a first rotational direction;
    means on the abductor member for enabling attachment to the other of the upper and lower brace portions;
    a stop member rotatably mounted in the housing member across the support surface and including a third abutment member extending adjacent the support surface to operatively contact the first abutment member to limit the relative movement of the abductor member in a second rotational direction; and
    means, integrally mounted on the housing member, for adjusting the rotatable position of the stop member relative to the housing member to define the extent of flexion and extension of the abductor member.

12. The hip orthosis of claim 11 wherein the abductor member has a U-shaped configuration.

13. The hip orthosis of claim 12 wherein the means on the abductor member includes an adjustable bracket member that can pivot relative to the U-shaped configuration.

14. The hip orthosis of claim 11 wherein the means for adjusting includes a screw member rotatably mounted on the housing member.

15. The hip orthosis of claim 14 wherein the stop member includes an annular gear member with teeth for engaging the screw member and the third abutment member is positioned at one end of the gear teeth.

16. The hip orthosis of claim 11, further including a measurement scale and indicator for setting the limits of movement of the abductor member.

17. An orthopedic hinge assembly for interconnecting an upper and a lower portion of a brace, comprising:
    a housing member having a first cylindrical cavity with a perimeter wall, the housing member having a second cylindrical cavity with a first opening in the perimeter wall between the first cylindrical cavity and the second cylindrical cavity, the perimeter wall having a second opening;

a first abutment member fixedly mounted in the cylindrical cavity;

means on the housing member for enabling attachment to a brace portion;

an abductor member movably mounted on the housing member to rotate across the cylindrical cavity;

a second abutment member, mounted on the abductor member and extending into the cylindrical cavity, to operatively contact the first abutment member to limit the relative movement of the abductor member in a first rotational direction, the second abutment member being of a size to pass through the second opening;

means on the abductor member for enabling attachment to another brace portion;

a stop member rotatably mounted in the cylindrical cavity;

a third abutment member, mounted on the stop member, to operatively contact the first abutment member to limit the relative movement of the abductor member in a second rotational direction; and adjustment means, integrally mounted in the second cylindrical cavity, for contacting and adjusting the rotatable position of the stop member relative to the housing member, to define the extent of flexion and extension of the abductor member.

18. The orthopedic hinge assembly of claim 17 wherein the abductor member has a U-shaped configuration.

19. The orthopedic hinge assembly of claim 18 wherein the means on the abductor member includes an adjustable bracket that can pivot in a transverse direction relative to a plane containing the first and second rotational directions.

20. The orthopedic hinge assembly of claim 17 wherein the stop member includes an annular gear member with teeth, the third abutment member is connected to the annular gear member, and the adjustment means includes a screw member rotatably mounted in the second cylindrical cavity for engaging the teeth of the gear member to define a worm gear assembly.

* * * * *